United States Patent
Loy et al.

(10) Patent No.: US 9,682,163 B2
(45) Date of Patent: Jun. 20, 2017

(54) METHOD AND APPARATUS FOR THE STERILIZATION OF PLASTICS MATERIAL PRE-FORMS WITH TEMPERED HOUSING

(71) Applicant: KRONES AG, Neutraubling (DE)

(72) Inventors: Michael Loy, Regensburg (DE); Juergen Soellner, Beratzhausen (DE); Hans-Peter Schiessl, Hohenburg (DE)

(73) Assignee: KRONES AG (DE)

( * ) Notice: Subject to any disclaimer, the term of this patent is extended or adjusted under 35 U.S.C. 154(b) by 0 days.

(21) Appl. No.: 14/614,947

(22) Filed: Feb. 5, 2015

(65) Prior Publication Data

US 2015/0231290 A1      Aug. 20, 2015

(30) Foreign Application Priority Data

Feb. 18, 2014   (DE) .................. 10 2014 102 031

(51) Int. Cl.
*A61L 2/00* (2006.01)
*A61L 2/18* (2006.01)

(52) U.S. Cl.
CPC ............. *A61L 2/18* (2013.01); *A61L 2202/23* (2013.01)

(58) Field of Classification Search
CPC ............................... A61L 2/18; A61L 2202/23
USPC ........................................................ 422/28
See application file for complete search history.

(56) References Cited

U.S. PATENT DOCUMENTS

| | | | |
|---|---|---|---|
| 6,692,684 B1 | 2/2004 | Nantin et al. | |
| 8,806,840 B2 | 8/2014 | Bierschneider | B67C 3/007 |
| 2002/0159915 A1* | 10/2002 | Zelina | A61L 2/186 422/3 |
| 2008/0152538 A1* | 6/2008 | Quetel | A61L 2/04 422/28 |
| 2009/0071104 A1 | 3/2009 | Fischer | 53/426 |
| 2013/0328248 A1 | 12/2013 | Herold et al. | |
| 2014/0014465 A1 | 1/2014 | Schoenberger et al. | |
| 2015/0027088 A1 | 1/2015 | Miyahara et al. | |

FOREIGN PATENT DOCUMENTS

| | | | |
|---|---|---|---|
| CN | 101193661 | 6/2008 | ............... A61L 2/20 |
| DE | 10 2005 012 507 A1 | 9/2006 | |
| DE | 10 2008 038 143 A1 | 2/2010 | |
| DE | 102009037172 | 2/2011 | ............. B65B 57/02 |
| EP | 2740678 A1 | 6/2014 | |

(Continued)

OTHER PUBLICATIONS

Extended European Search Report dated Jun. 26, 2015 for Application No. 15155647.9.

(Continued)

*Primary Examiner* — Kevin Joyner
(74) *Attorney, Agent, or Firm* — Hayes Soloway P.C.

(57) ABSTRACT

A method and apparatus for the sterilization of plastics material pre-forms, wherein the plastics material pre-forms are conveyed by a conveying device along a pre-determined conveying path and are sterilized at least for a time during this conveying by being acted upon with a flowable sterilization agent, wherein the plastics material pre-forms are conveyed at least for a time inside a housing. According to the method and apparatus, at least one portion of the housing is heated at least for a time and/or during the sterilization procedure by a heating source independent of the sterilization agent.

17 Claims, 1 Drawing Sheet

(56) References Cited

FOREIGN PATENT DOCUMENTS

| | | |
|---|---|---|
| EP | 2826716 A1 | 1/2015 |
| WO | 2013021882 A1 | 2/2013 |
| WO | 2013137321 A1 | 9/2013 |
| WO | 2013137325 A1 | 9/2013 |

OTHER PUBLICATIONS

Chinese First Office Action (w/translation) issued in application No. 2015100708575, dated Nov. 18, 2016 (20 pgs).

* cited by examiner

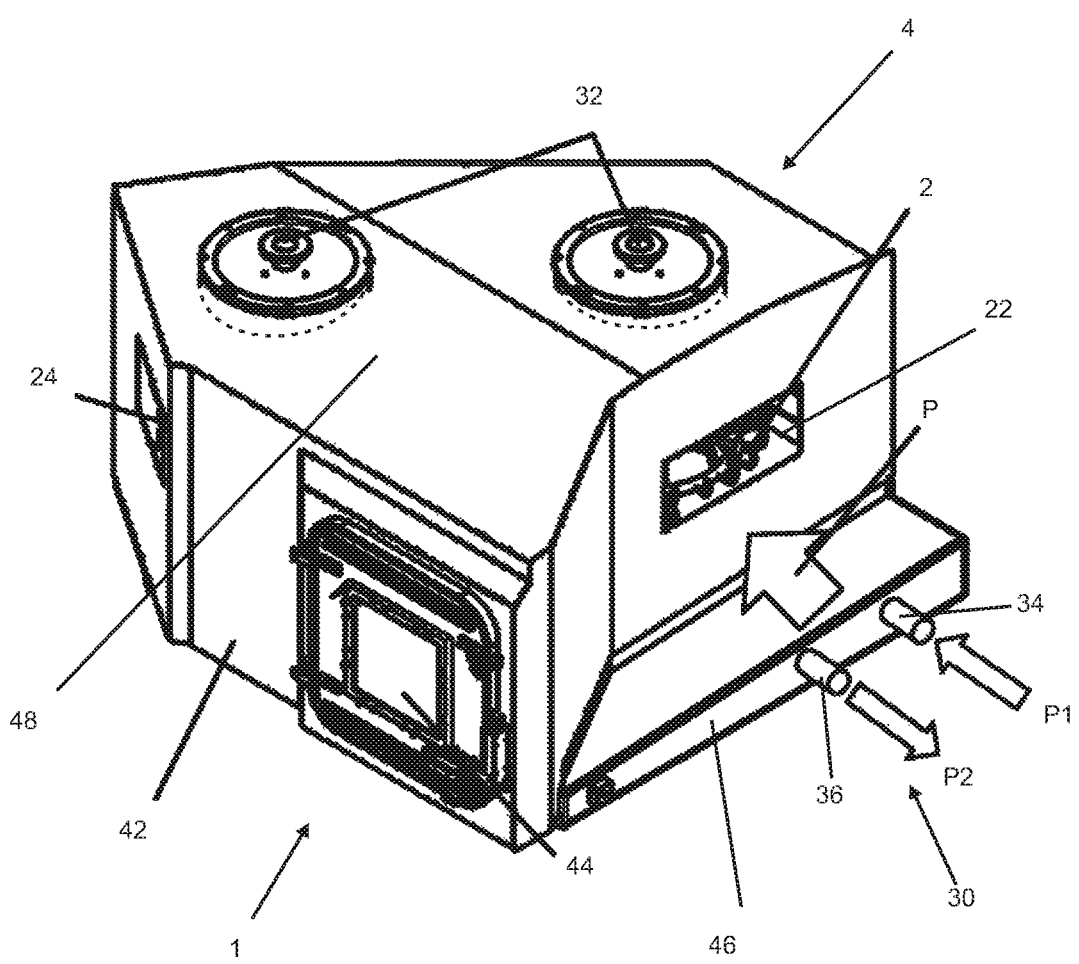

METHOD AND APPARATUS FOR THE STERILIZATION OF PLASTICS MATERIAL PRE-FORMS WITH TEMPERED HOUSING

BACKGROUND OF THE INVENTION

The present invention relates to a method and an apparatus for the sterilization of plastics material pre-forms. It is generally known in the field of the drinks production industry that plastics material pre-forms are first made available, and they are then heated in a furnace and are expanded to form plastics material containers by means of blow moulding machines for example.

In this case, in numerous applications or beverages to be filled respectively it is advantageous or necessary for the containers themselves to be sterilized. In particular, the durability of sensitive filling products, in particular in PET bottles, can be decisively improved if the number of germs in the containers is significantly reduced before the filling process. To this end, different wet and dry aseptic methods are known in the field of filling technology. A fundamental drawback with these methods lies in the fact that on account of the large volumes of the containers they require a high consumption of sterilization medium (such as for example peracetic acid or hydrogen peroxide). More recent machine concepts are therefore based upon the fact that the number of the germs is already reduced before the blow moulding of the containers in a blow moulding machine. In other words, the plastics material pre-forms or "pre-forms" (English term) respectively are sterilized in this case. For this purpose the plastics material pre-form passes through a treatment region in which the disinfection is achieved, in particular, by gaseous or liquid sterilization agents or even by irradiation (for example with UV or electron radiation).

If a gaseous sterilization agent such as for example $H_2O_2$ is used for the disinfection, then this aggregate state has to be maintained in the treatment region during the entire disinfection process. Only in this way a constantly high concentration of the sterilization medium and, as a result, a robust disinfection process with a constantly high disinfection rate can be ensured.

In particular, however, the housing wall of a treatment room also constitutes a problem with this type of sterilization. In order that the concentration of the sterilization agent should remain constant, it should namely be ensured that the temperature does not drop below the dew point of the mixture at any point.

In the prior art it is customary for this tempering of the wall also to be achieved directly by the sterilization medium or the temperature thereof respectively. This means that the process gas supplied to the sterilizer is set so high that a corresponding tempering of the treatment region or even the walls respectively can be achieved. This leads, however, to an unnecessarily high energy consumption and to a high thermal loading of the mechanical components.

The object of the present invention is therefore to reduce the energy consumption of apparatus of this type. In addition, an excessively high stressing of the individual components of apparatus of this type should preferably also be avoided.

SUMMARY OF THE INVENTION

In the case of a method according to the invention for the sterilization of plastics material pre-forms the plastics material pre-forms are conveyed by a conveying device along a pre-determined conveying path and are sterilized at least for a time during this conveying by being acted upon with a flowable sterilization agent. In this case the plastics material pre-forms are conveyed at least for a time inside a housing.

According to the invention at least one portion of the housing is heated at least for a time before and/or during the sterilization procedure by a heating source independent of the sterilization agent. As an alternative or in addition, as well as the heating it is possible for at least one sterilization region, in which the plastics material pre-forms are sterilized, to be thermally insulated with respect to an environment. It is preferable for this heating to take place at least also for a time and preferably continuously during the sterilization procedure. In this case the sterilization procedure is understood as being, in particular, the stressing of the plastics material pre-forms with the sterilization medium. In conjunction with the stressing the sterilization medium can be applied in an active manner (for example with spraying units) to the plastics material pre-forms or can also be poured into them. It would also be possible, however, for the plastics material pre-forms to be conveyed only through an atmosphere which contains the sterilization agent. The additional or alternative thermal insulation is based upon the concept that it would be possible for example for this room to be heated once and for this temperature level to be maintained by the thermal insulation. In addition, it would be possible for a specific adequate temperature level to be maintained more easily by this thermal insulation. In this way for example, the boundary walls of the housing could also be produced from a thermally insulating material. In this way, a material with a multiplicity of layers could be used for example for walls of the housing.

It is preferable, however, for the plastics material pre-forms to be acted upon with the sterilization agent at least for a time by means of stressing device[s] such as for example nozzle elements. It is preferable in this case for these stressing devices to be jointly moved at least for a time with the plastics material pre-forms to be sterilized. In the scope of the sterilization procedure it is preferable for at least also one internal surface of the plastics material pre-forms to be acted upon with the sterilization agent. In this case it would be possible for stressing devices of this type to be introduced at least in part into the plastics material pre-forms. As an alternative or in addition, it is also possible, however, for an external surface of the plastics material pre-forms to be acted upon with the sterilization agent.

It would also be possible, however, for a heating to be started before the actual sterilization procedure, for example within the scope of a pre-heating. As well as the (wall) portions of the housing it is possible for other regions of the apparatus to be heated, such as for example carriers for a sterilization wheel, guides, treatment elements and the like. This heating could then be maintained more easily by means of the thermal insulation.

As already mentioned above, the concentration of the sterilization medium is determined by a fixed ratio between the quantity of sterilization agent, for example $H_2O_2$, and a quantity of hot air. The hot air acts in this case as a carrier medium for the sterilization agent. The higher the concentration of sterilization agent, such as for example $H_2O_2$, in the air, the higher also the dew point of this mixture. In order that the concentration in the treatment region remains constant, at no point the local temperature should drop below the dew point of the mixture.

The sterilization agent, such as $H_2O_2$, would then in fact condense out and, as a result, the concentration would drop. In the case of apparatus from the prior art, on account of the poor heat transmission between the process gas and the housing of the treatment region an air temperature is necessary which is substantially higher than what would be necessary for the conveying of $H_2O_2$.

The invention now proposes that the aforesaid housing regions, and in particular the housing walls, should be heated independently of the sterilization agent or a separate heating of the treatment region should be provided respectively and/or at least one specified temperature level should be maintained by the thermal insulation. On account of this functional separation of the two tasks of heating the treatment region and the gaseous conveying of the hydrogen peroxide or the sterilization agent respectively or on account of the thermal insulation, the two functions can also be individually optimized.

This procedure makes it possible for the temperature in the process gas, i.e. in particular the flowable sterilization agent, to be capable of being lowered to the level necessary for conveying the sterilization agent, such as for example hydrogen peroxide. In this way, the thermal loading of the individual component parts of the apparatus is also reduced. It is pointed out in this context that the flowable sterilization agent can be both the actual agent itself, such as for example hydrogen peroxide, and a mixture between hot air and the agent. It is advantageous for the flowable sterilization agent to be produced by a mixing procedure.

In particular, this is a mixing procedure between a sterilization agent (likewise flowable), such as—in particular but not exclusively—$H_2O_2$, and a further flowable, in particular gas-compatible, medium, and in particular air, and in a particularly preferred manner sterile air.

By means of the procedure according to the invention the housing of the treatment region can be tempered separately with heating means. The latter can have a considerably better heat transmission in this case. In this way, the heating method becomes more effective and the efficiency is also increased as a whole.

In the case of a further advantageous embodiment the sterilization agent is a sterilization agent in the form of a gas or vapour. It is advantageous for the sterilization agent to be hydrogen peroxide or a hydrogen peroxide mixture respectively. It is advantageous for the sterilization agent, and in particular the hydrogen peroxide, to be kept at a temperature or to be brought to a temperature which is just sufficient for the gaseous conveying of the sterilization agent or the agent respectively.

The invention is described and claimed here with reference to plastics material pre-forms. It is also pointed out, however, that the invention can be applied to the sterilization of other containers, such as for example plastic bottles, glass bottles and the like. In addition, the invention can also be applied to the sterilization of container closures.

In the case of a preferred arrangement of the method the aforesaid portion is acted upon with a further flowable medium. This can be, in particular, heated or hot air which is applied to this portion. In this case it is possible for the stressing of the wall to start at a point in time at which the sterilization process has not yet started. In this way, it is advantageous for a pre-tempering of the sterilization region or of the housing respectively to be carried out. It is preferable for the portion of the housing to be at least one housing wall (or a cover wall or a base wall respectively). It would also be possible, however, for a plurality of or all of the housing walls to be heated. In addition, other elements of the housing can be heated, such as for example windows fitted in the housing. In addition, it is possible for these housing walls to have openings, for example in order to supply or remove containers. It would also be possible for a multiplicity of technical principles to be used before the heating of the portions, such as for example an electrical heating of windows and a heating of other wall portions by means of heated air.

Alternatively, however, electrical heating devices could also be used. In addition, a heating with a liquid medium and/or a medium in the form of a vapour would be possible.

In this way, it would be possible for example for separate heating devices to be installed in the treatment region, such as for example heated windows. It is advantageous for the heated flowable medium to be removed from a further apparatus for the treatment of plastics material pre-forms. As already mentioned above, in the case of apparatus from the prior art it is known for these to have a plurality of parts of the plant—usually arranged one behind the other. Some of these parts of the plant, such as in particular the furnaces by which the plastics material pre-forms are heated, emit waste heat to a substantial degree in this case.

In this way, as mentioned above, it would be possible for example to make use of the waste heat of the heating furnace of a stretch blow moulding machine, in which case the heated medium can preferably arrive at the sterilization device by way of suitable pipelines or guide plates for this purpose. The waste heat of this heating furnace has a usable temperature level of from approximately 30° C. to 60° C. If this temperature level were transferred to the treatment region, then the temperature of the sterilization medium could be lowered to a level of from approximately 90° C. to 110° C. In this way, the warm waste air, preferably that of the heating furnace, is supplied in this case to the sterilization device for heating purposes and, in particular, it can be cleaned in order to improve the hygiene of the surroundings. As well as the furnace mentioned here for heating the plastics material pre-forms, however, other machines can be used or use can be made of the waste heat thereof respectively. In this way for example, the waste heat of a high-power compressor of a blow moulding machine can likewise and/or additionally be used.

In addition, a multiplicity of further parts of the plant can also be used jointly or at the same time respectively as a source for a heated medium.

In a further advantageous embodiment the plastics material pre-forms are sterilized inside a clean room. This clean room can preferably be closed off in this case by the housing mentioned above. In this case sluice devices can be provided in order to supply the plastics material pre-forms to the heating room.

In the case of a further advantageous embodiment a profile of the housing can be adapted to a profile of the conveying path of the plastics material pre-forms.

In this way, a minimization of the area of the wall portion to be heated can be achieved. A wall portion to be heated can also be a base portion or cover portion.

In general, it is preferable for the heated flowable medium to be cleaned before it arrives at the wall portion to be heated. In this way, account is taken of the fact that the sterilization is usually carried out inside a clean room. High-efficiency particulate air filters (for example H 14) can be used for example for cleaning this medium. This cleaning also leads to a significantly lower concentration of micro-organisms, in particular in the region of the inlet of the sterilization device. It is preferable, however, for a heat source, which is situated in the immediate machine vicinity of the sterilization device, to be used for heating the portion.

In the case of a further advantageous embodiment at least one sterilization region, in which the plastics material pre-forms are sterilized, is thermally insulated with respect to an environment. In particular, the wall portions specified above, which bound at least this sterilization region, are thermally insulated with respect to an environment. This can be carried out in a simple manner for example in that the wall to be heated is separated from a further outer wall by means of a layer of air.

In order to be able to keep the heat introduced in the treatment region in an improved manner, it is advisable, in addition to the warming or heating respectively, for the entire region to be insulated towards the outside. As well as the lower heat losses there is a further advantage in that the influence of the ambient temperature upon the sterilization conditions is minimized. In this way, the entire sterilization process is also independent of temperature fluctuations, for example seasonal temperature fluctuations.

The present invention further relates to an apparatus for the sterilization of plastics material pre-forms, which has a conveying device which conveys the plastics material pre-forms along a pre-set conveying path. In addition, the apparatus has at least one stressing device, which acts upon the plastics material pre-forms with a flowable medium for the sterilization thereof, as well as a housing which surrounds the conveying path of the plastics material pre-forms at least in sections. According to the invention the apparatus has a heating device which heats at least one wall portion of the housing, at least for a time. In addition, or as an alternative, at least one portion of the housing, which surrounds the conveying path of the plastics material pre-forms, is thermally insulated from the environment of the apparatus.

It is therefore preferable for at least one wall, which bounds the conveying path of the plastics material pre-forms, to be designed so as to be thermally insulating. In this way for example, multiple-component walls with layers of air situated between them could be used for the thermal insulation. In addition, it is possible for a closed-cell foam of synthetic rubber to be stuck on.

In this case, in particular, this heating device is independent of the stressing device or the stressing device is not also used for heating the housing or a portion of the housing respectively.

In the case of a further advantageous embodiment the apparatus has a further stressing device which acts upon the wall portion of the housing with a further flowable medium for the heating thereof. This can be for example a supply device for supplying warm air which strikes the respective walls.

It is also possible, however, to use an electrically operated heating device or a heating device fed by a heated liquid.

The present invention further relates to a plant for the production of plastics material containers with an apparatus of the type described above as well as a further apparatus for the treatment of plastics material containers. In this case the plant has a connection line in order to transfer a heated medium from this further apparatus to the apparatus. In the case of this design it is therefore proposed that heat, in particular waste heat of a further apparatus, should be used to heat the housing walls for their part.

BRIEF DESCRIPTION OF THE DRAWINGS

Further advantages are evident from the accompanying drawing. In the drawing

The FIGURE is a diagrammatic illustration of an apparatus according to the invention.

DETAILED DESCRIPTION OF THE INVENTION

The FIGURE is a diagrammatic illustration of an apparatus 1 according to the invention for the sterilization of plastics material pre-forms. This apparatus has a first supply opening 22 by way of which the containers, i.e. in this case the plastics material pre-forms, can be supplied to the apparatus (arrow P). The reference number 2 designates a conveying device which conveys the plastics material pre-forms inside the apparatus 1. This conveying device 2 preferably has in this case at least one conveying wheel on which are arranged a plurality of holding elements for holding the plastics material pre-forms. In this way, the plastics material pre-forms are preferably conveyed onto a circular conveying path. In addition, however, a plurality of conveying devices, in particular a plurality of conveying star wheels, could be arranged in the housing 4, in which case the plastics material pre-forms transfer for example from an inlet star wheel to a further conveying star wheel and from there further to an outlet star wheel.

The reference number 24 designates a removal opening or an outlet respectively in order to remove the plastics material pre-forms (now sterilized). It is preferable for the supply opening 22 to be arranged in a manner spatially separated from the removal opening.

The housing 4 forms in the interior thereof a clean room, inside which the plastics material pre-forms are sterilized. The reference number 32 refers to supply openings in order to supply a process gas, i.e. in this case in particular a mixture of hydrogen peroxide and air, to the housing. Nozzle elements, which act upon the plastics material pre-forms with the sterilization medium in a purposeful manner, can be arranged in the interior of the housing. The interior of the housing thus also constitutes an insulated treatment region.

The reference number 44 refers to a window through which the user can look into the interior of the apparatus 1. This window can also preferably be opened in this case and can thus expose an inspection opening.

The reference number 42 designates by way of example a first wall and the reference number 46 a further wall—in this case a base of the apparatus. In the case of the illustration reproduced in the FIGURE this base can be heated by the supply of a tempering medium. For this purpose a supply line 34 is provided, by way of which the tempering medium is supplied along the arrow P1. The reference number 36 designates a return line for the removal of the tempering medium. The base 46 also acts therefore as a heat exchanger and, by means of this supplied air, which can originate for example from another apparatus (not shown), it can be used for heating purposes. The reference number 48 designates a cover or a cover wall respectively of the apparatus.

Furthermore, it would be possible for drives for the conveying device 2 to be arranged not inside the housing 4 or the clean room respectively but outside the housing. In addition, sterilization elements can also be provided which for example also sterilize regions of the conveying device itself, such as for example the gripping clamps which hold the plastics material pre-forms. In addition, however, it would also be possible for a sterilization of such parts of a plant to be carried out prior to an actual operating mode.

The heating medium, which is supplied by way of the supply opening or the tube 34 respectively and is removed by way of the removal opening or the tube 36 respectively, is thus conveyed exclusively inside the wall element 46 in the embodiment shown here and it preferably does not therefore reach the interior of the housing itself. It would also be possible, however, for this heated medium also to be distributed in the interior of the housing, in order to be able to heat other walls in this way, such as in this case the wall 42. In this way, distribution devices such as nozzle elements, which act upon the walls with the warm air in a purposeful manner, could be provided for example in the interior of the housing. In addition, guide channels for air could also be arranged inside the walls, in order to act upon the latter in this way. In this case the wall portions are acted upon from the inside.

The reference number 30 refers to the heating device in its entirety, which in the case of the embodiment shown here has the two lines 34 and 36 as well as the wall portion 46 to be heated.

All the features disclosed in the application documents are claimed as being essential to the invention, insofar as they are novel either individually or in combination as compared with the prior art.

LIST OF REFERENCES

1 apparatus
2 conveying device
4 housing
22 supply opening
24 removal opening
30 heating device
32 supply opening
36 return line, removal opening
42 first wall
44 window
46 further wall
P, P1, P2 arrows

The invention claimed is:

1. A method for sterilization of plastics material pre-forms, wherein the plastics material pre-forms are conveyed by a conveying device along a pre-determined conveying path and are sterilized at least for a time during this conveying by being acted upon with a flowable sterilization agent, wherein the plastics material pre-forms are conveyed at least for a time inside a housing, wherein;
    at least one portion of the housing is heated at least for a time before and/or during the sterilization procedure by a heating source independent of the sterilization agent; and
    the sterilization procedure being stressing the plastic material pre-forms with the flowable sterilization agent; and/or
    at least one sterilization region, in which the plastics material pre-forms are sterilized, is thermally insulated with respect to an environment, the sterilization region being tempered separately with the heating source which directly heats an exterior surface of at least one wall portion of the housing.

2. The method according to claim 1, wherein the portion acted upon with a further heated flowable medium.

3. The method according to claim 2, wherein the heated flowable medium is removed from a further apparatus for the treatment of plastics material pre-forms.

4. The method according to claim 3, wherein a further apparatus is an apparatus for the heating of plastics material pre-forms.

5. The method according to claim 2, wherein the heated flowable medium is cleaned before it arrives at the portion.

6. The method according to claim 1, wherein the plastics material pre-forms are sterilized inside a clean room.

7. The method according to claim 1, wherein at least one portion of the housing is heated at least for a time before and/or during the sterilization procedure by a heating source independent of the sterilization agent, and/or the housing, in which the plastics material pre-forms are sterilized, is thermally insulated with respect to an environment.

8. The method according to claim 1, wherein the interior of the housing constitutes a thermally insulated region.

9. The method according to claim 8, wherein the directly heated wall portion is thermally insulated from the environment.

10. An apparatus for the sterilization of plastics material pre-forms, with a conveying device, which conveys the plastics material pre-forms along a pre-set conveying path, with at least one stressing device, which acts upon the plastics material pre-forms with a flowable medium for the sterilization thereof, and with a housing, which surrounds the conveying path of the plastics material pre-forms at least in sections, wherein;
    the apparatus has a heating device, which directly heats the exterior surface of at least one wall portion of the housing at least for a time before and/or during a sterilization procedure; and
    the sterilization procedure being stressing the plastic material pre-forms with the flowable medium for the sterilization; and/or
    a portion of the housing is thermally insulated from the environment of the apparatus, the portion of the housing being tempered separately with the heating device.

11. The apparatus according to claim 10, wherein the apparatus has a further stressing device which acts upon the wall portion of the housing with a further flowable medium for the heating thereof.

12. The apparatus according to claim 10, wherein the apparatus has a heating device, which heats at least one wall portion of the housing at least for a time, and/or the housing is thermally insulated from an environment of the apparatus.

13. The apparatus according to claim 10, wherein the interior of the housing constitutes a thermally insulated region.

14. The apparatus according to claim 13, wherein the directly heated wall portion is thermally insulated from the environment.

15. A plant for the production of plastics material containers with an apparatus according to claim 11 as well as a further apparatus for the treatment of plastics material containers, wherein the plant has a connection line in order to convey a heated flowable medium form this further apparatus to the apparatus.

16. The plant according to claim 15, wherein the interior of the housing constitutes a thermally insulated region.

17. The plant according to claim 16, wherein the directly heated wall portion is thermally insulated from the environment.

* * * * *